United States Patent [19]
Dakin, Jr. et al.
[11] 4,012,614
[45] Mar. 15, 1977

[54] HIGH-VOLTAGE CIRCUIT-INTERRUPTER HAVING A CLOSING RESISTANCE AND IMPROVED SHUNTING-RESISTANCE CONTACTS THEREFOR

[75] Inventors: Hayes O. Dakin, Jr.; Lawrence A. Brunson, both of Irwin, Pa.; Frank L. Reese, deceased, late of Monroeville, Pa.; by Blanche C. Reese, executrix, Lansford, Pa.

[73] Assignee: Westinghouse Electric Corporation, Pittsburgh, Pa.

[22] Filed: Dec. 17, 1973

[21] Appl. No.: 425,670

[52] U.S. Cl. .................... 200/144 AP; 200/148 R; 200/145

[51] Int. Cl.$^2$ ........................................ A01H 33/16

[58] Field of Search ..... 200/144 AP, 148 R, 148 F, 200/145

[56] References Cited

UNITED STATES PATENTS

| | | | |
|---|---|---|---|
| 3,287,531 | 11/1966 | Yonezawa et al. | 200/144 AP |
| 3,291,947 | 12/1966 | Van Sickle | 200/144 AP |
| 3,538,276 | 11/1970 | Leeds | 200/144 AP |
| 3,596,028 | 7/1971 | Kane et al. | 200/148 R |
| 3,665,133 | 5/1972 | Reese et al. | 200/148 R |

*Primary Examiner*—Robert S. Macon
*Attorney, Agent, or Firm*—W. R. Crout

[57] ABSTRACT

An improved high-voltage circuit-interrupter is provided having series main contacts and resistance contacts with a closing resistance shunting the resistance contacts, so that the closing resistance is inserted into the circuit during the closing operation of the high-voltage circuit-interrupter, but is out of the circuit during the opening operation. An improved latching mechanism is provided for ensuring that the resistance contacts remain closed, during the beginning of the opening operation of the breaker, so that the closing resistance is shorted out, and the task of extinguishing the established arc, or arcs is imposed only upon the main contacts and not at the resistance contacts.

During the closing operation, the construction is such that the main driving frame, carrying the movable main contact or contacts, charges a biasing means, but latches, which are provided, ensure that the main contacts are closed prior to the closing of the serially-related resistance contacts, thereby inserting the closing resistance into the circuit momentarily during the closing operation of the high-voltage circuit-interrupter.

Another very important feature of the invention is the provision of an encircling closing resistance encompassing, or surrounding the separable closing contacts as a space-saving and cost-reduction constructional arrangement. Moreover, an additional feature of the invention is the provision of a probe contact, when desired, to short out the closing resistance in two steps, rather than shorting it out in one step. Thus, the individual resistance steps may be individually calculated for the optimum closing resistance value.

12 Claims, 22 Drawing Figures

HIGH-VOLTAGE CIRCUIT-INTERRUPTER HAVING A CLOSING RESISTANCE AND IMPROVED SHUNTING-RESISTANCE CONTACTS THEREFOR

CROSS-REFERENCES TO RELATED APPLICATIONS

References may be made to U.S. Patent application filed Dec. 4, 1973, Ser. No. 421,574, now U.S. Pat. No. 3,863,041, issued Jan. 28, 1975 to Joseph R. Rostron and Sylvester J. Dropik and assigned to the assignee of the instant application, which shows an alternate mechanism arrangement for controlling the insertion of a closing resistance and the control of the resistance contacts during the opening operation, so that the extinguishing action occurs only at the main contact or contacts and not at the resistance contacts during such an opening operation of the breaker.

BACKGROUND OF THE INVENTION

In U.S. Pat. No. 3,291,947, issued Dec. 13, 1966 to Roswell C, Van Sickle, and assigned to the assignee of the instant application, there is described the function, purpose and desirable ohmic values of a closing resistance, which is inserted into the circuit only during the closing operation of the breaker, and which is out of the circuit, that is, shorted out of the circuit, during the opening operation of the breaker. In this U.S. Pat. No. 3,291,947, there is illustrated a rotating bridging type of separable main contact structure with an auxiliary resistance contact associated with each stationary contact, so arranged that the closing resistance, of a desirable specified ohmic value, is inserted into the controlled circuit at a predetermined time during the closing operation, and is ultimately shorted out in the fully-closed-circuit position of the interrupter.

During the opening operation of the aforesaid circuit-interrupter, as described in the aforesaid Van Sickle U.S. Pat. No. 3,291,947, the arrangement is such that the closing resistance is out of the circuit during the opening operation, and the extinguishing action, or arc interruption, occurs only at the separable rotating main contact structure and not at the closing-resistance contacts, which obviously is desirable.

In the aforesaid Van Sickle U.S. Pat. No. 3,291,947, there is claimed ranges of ohmic resistance values, which have been found to damp, or to entirely eliminate undesirable voltage surges on the controlled line during the closing operation of the circuit-interrupter. This is desirable inasmuch as the existence of high-voltage surges on the controlled line imposes unnecessary voltage stress on the insulation equipment of the line, and creates the concurrent hazard of flashover across such supporting insulating structures or equipment.

SUMMARY OF THE INVENTION

In accordance with the present invention there is provided serially-related separable main contacts and separable resistance contacts, with a closing resistance in shunt with the separable resistance contacts. The construction is such that the one or more main contacts are closed during the closing operation, whereas the movable resistance contact is latched open until the appropriate time during such a closing operation, whereby the resistance is shorted out of the circuit in one or two steps, as desired. Suitable means are provided for unlatching the movable resistance contact, and thereby permitting it to close, thus shorting out the resistance in the fully-closed circuit position of the interrupter. Thus, the main contacts are closed prior to a subsequent closing of the resistance contacts, so that, in effect, the closing resistance is inserted, into the circuit momentarily during the closing operation of the interrupter in one or two steps, as desired.

During the opening operation of the interrupter, on the other hand, it is desirable to have the closing resistance out of the circuit, and to impose the extinguishing action, or arc-interruption burden only at the main separable contacts and not at the separable resistance contacts to avoid burning and arc erosion at the resistance contacts. To achieve this end, there is provided an improved latching arrangement such that in both the opening and closing operations of the circuit-interrupter, suitable latches are provided to latch the movable resistance contact in either its closed position, during the opening operation of the interrupter, so that the resistance is out of the circuit during opening, and arc extinction occurs only at the one or more main contacts. Additionally, during the closing operation, the movable resistance contact is latched in its open position, thereby momentarily inserting the resistance in one or two steps, as desired during such a closing operation of the interrupter.

Additionally, the arrangement is such that the resistance structure itself encircles, or generally surrounds, the separable resistance contacts to provide a desired voltage shielding arrangement so that the high-voltage gradient conditions are improved.

Further objects and advantages of the invention will readily become apparent upon reading the following specification taken in conjunction with the drawings.

DESCRIPTION OF THE PREFERRED EMBODIMENT

Figure 1:
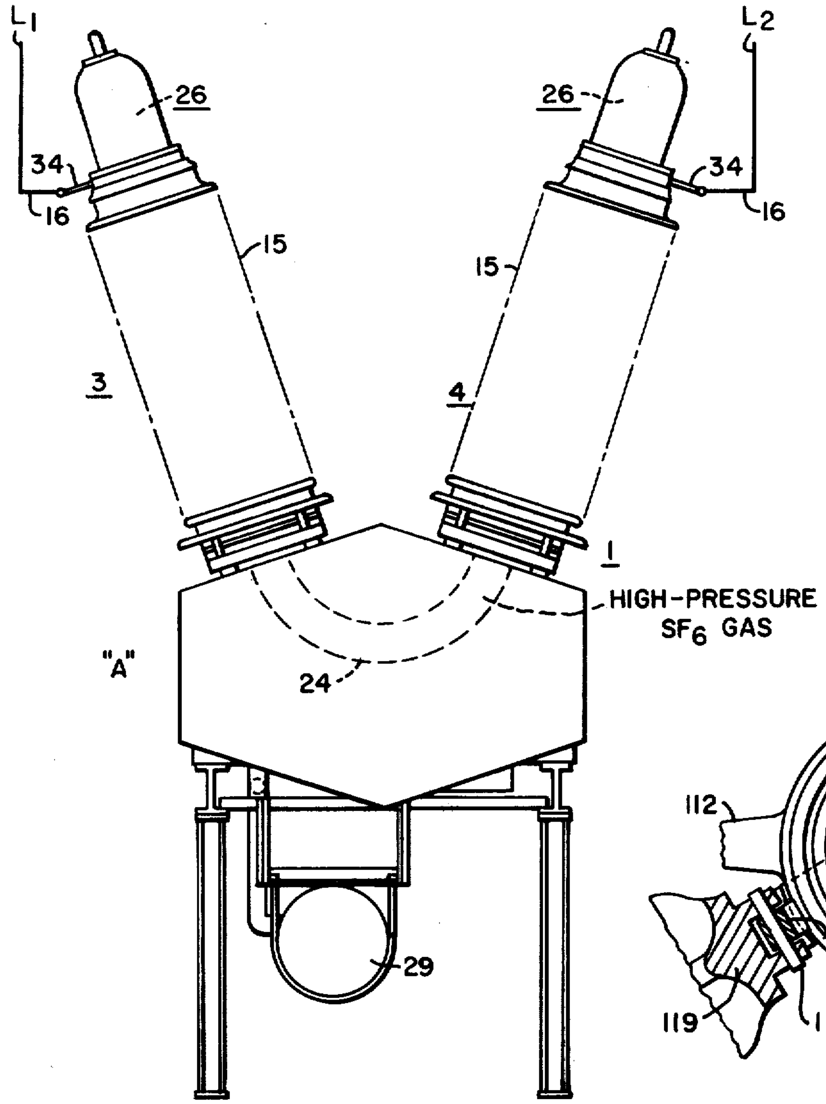
FIG. 1 is an end elevational view of a three-phase circuit-interrupter of the gas-blast type embodying the principles of the present invention.
Figure 14:
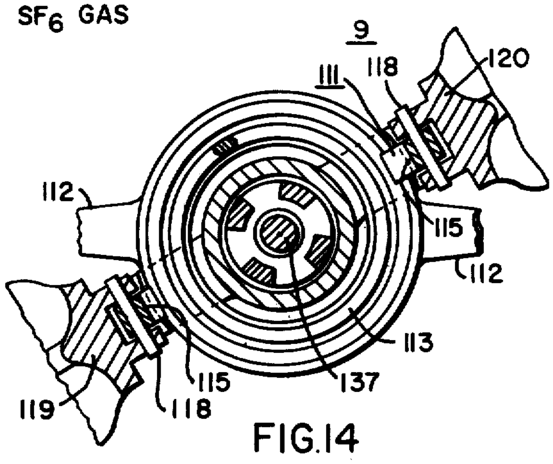
FIG. 14 is a plan view, in section, taken substantially along the line XIV—XIV of FIG. 7C.

Referring to the drawings, and more particularly to FIGS. 1–4 of the drawings, it will be noted that there is illustrated a three-phase high-voltage circuit-interrupter of the gas-blast type 1, such as set forth in U.S. Pat. No. 3,596,028, many detailed component parts of which are described in said patent, and also in the patents referred to in said U.S. Pat. No. 3,596,028. Various details of the operating structure may be gleaned from a reading of the aforesaid U.S. patent and the patents therein referred to. However, for an understanding of the present invention, it is merely necessary to know that each column structure 3, 4 contains two main arc-extinguishing units 6 and 7 together with a lower resistance unit 9, which has the resistance contacts 11, 12 thereof controlled in such a manner that during the closing operation of the interrupter 1, the closing resistance 14 is inserted serially into the circuit to damp any high voltage surges occurring on the line 16 (FIG. 1). However, as will be obvious, in the fully closed-circuit position of the interrupter 1, it is desirable to shunt, or to take the resistance 14 out of the circuit due to heating effects and energy losses, and the function of the separable closing contacts 11, 12 is to achieve this end.

During the opening operation, on the other hand, it is desirable to have the resistance 14, which serves only a closing function, completely out of the circuit 16 during the opening operation. As a result, the closing resistance 14 is shunted out of the circuit 16 during the initial portion of the opening operation, where the task of interrupting the arcs 18, 19 is imposed only on the main contact structures 21, 22, and not at the resistance-contact structure 11, 12. In the particular embodiment under discussion, and as illustrated in FIGS. 1–4, there are provided two main contact structures 21, 22 and a lower serially-related resistance contact structure 11, 12 on each slanting column structure 3, 4, such as illustrated in FIG. 1. Reference may be made to the diagrammatic view of FIG. 8 for an indication of the fact that there are provided six breaks through the entire circuit 16 from $L_1$, through the two main contact structures 21 and 22 of the left-hand column 3, through the lower resistance contact structure 11, 12 of the left-hand column 3, through a generally U-shaped conductor tube 24 (FIG. 1), and through the right-hand slanting column structure 4, in a similar manner, to the upper line terminal $L_2$ of the interrupter 1.

With further reference to FIG. 1 of the drawings, it will be observed that there are provided two identical interrupting assemblages 3 and 4 slantingly arranged away from each other, as illustrated in FIG. 1, and each of which contains two serially-related main contact assemblages 21, 22, together with a serially-related separable resistance contact assemblage 13, which controls the insertion of the closing resistance 14.

Figure 5A:
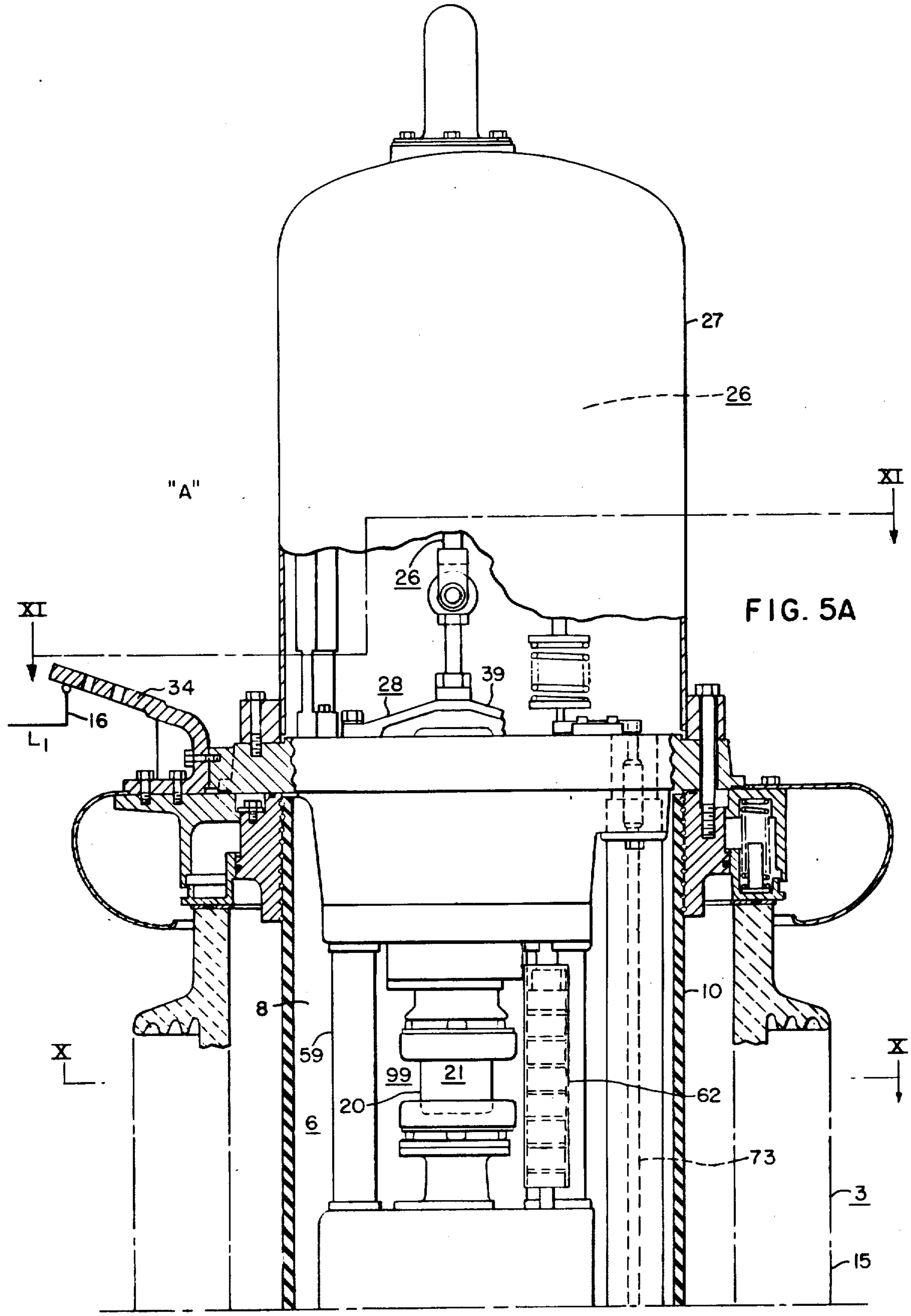
FIG. 5A is an enlarged side-elevational view, partially in vertical section, of the upper main arc-extinguishing unit of one-half of a pole-unit of the breaker, the contact structure being illustrated in the closed-circuit position.

Disposed at the upper end of the columnar assemblage 3 of FIG. 5A is an operator, or driving mechanism 26, more fully illustrated in U.S. Pat. No. 3,590,189, issued June 29, 1971 to Fischer et al, and assigned to the assignee of the instant application. To understand the present invention, however, it is only necessary to know that downward movement of the operator, generally designated by the reference numeral 26 in FIG. 5A, effects closing downward operation of the contact structures 13, 21 and 22. Conversely, upward linear movement of the operator 26, together with the main frame assembly 28, comprising the operating rods 30, 31 of FIG. 6A, will cause opening movement of the main contact structures 21 and 22.

Figure 7A:
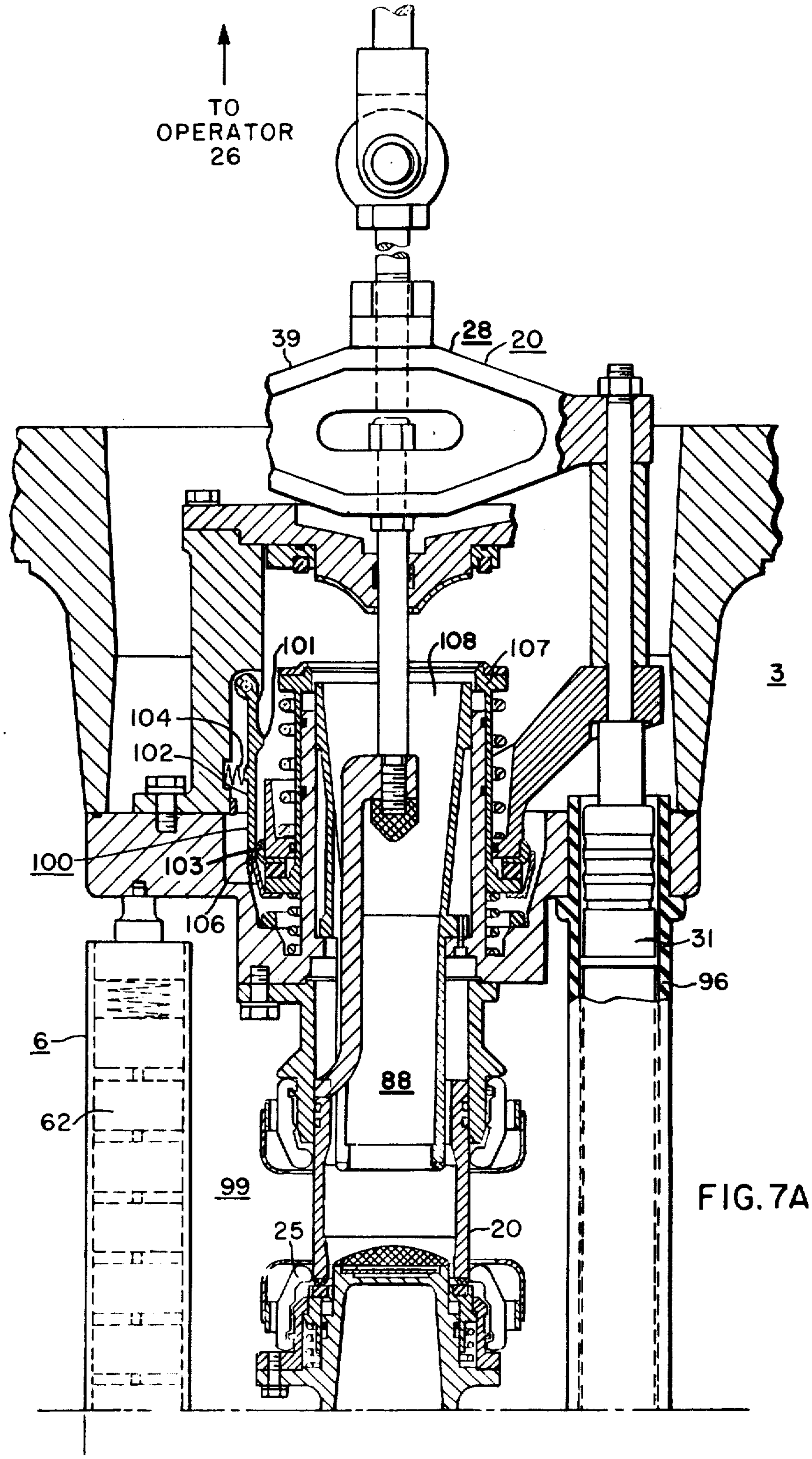
FIG. 7A is an enlarged vertical sectional view taken through the upper arc-extinguishing unit of the structure illustrated in FIG. 5, again with the contact structure being illustrated in the closed-circuit position.
Figure 7B:
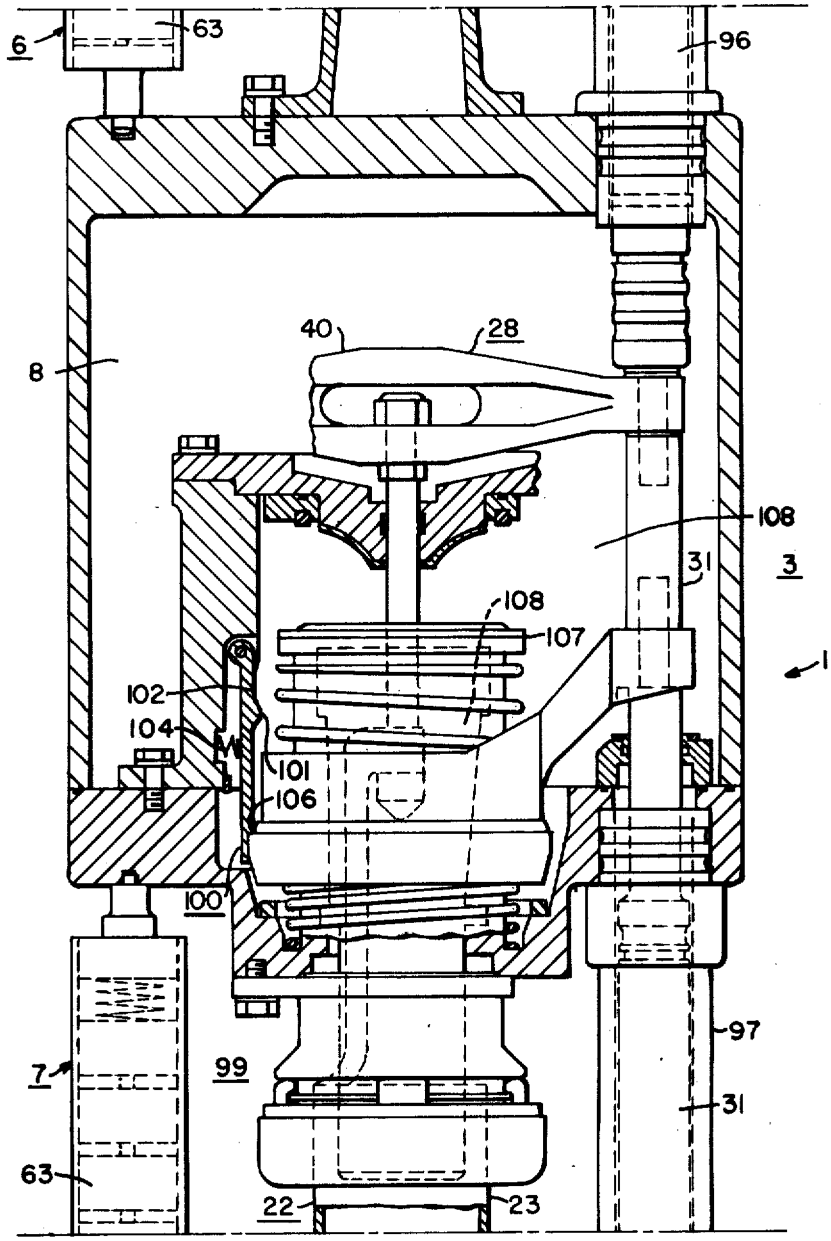
FIG. 7B is a generally vertical sectional view taken through the second main contact structure of the arc-extinguishing unit disposed immediately below the upper arc-extinguishing unit, illustrated in FIG. 7A, again the contact structure being illustrated in the closed-circuit position.
Figure 7C:
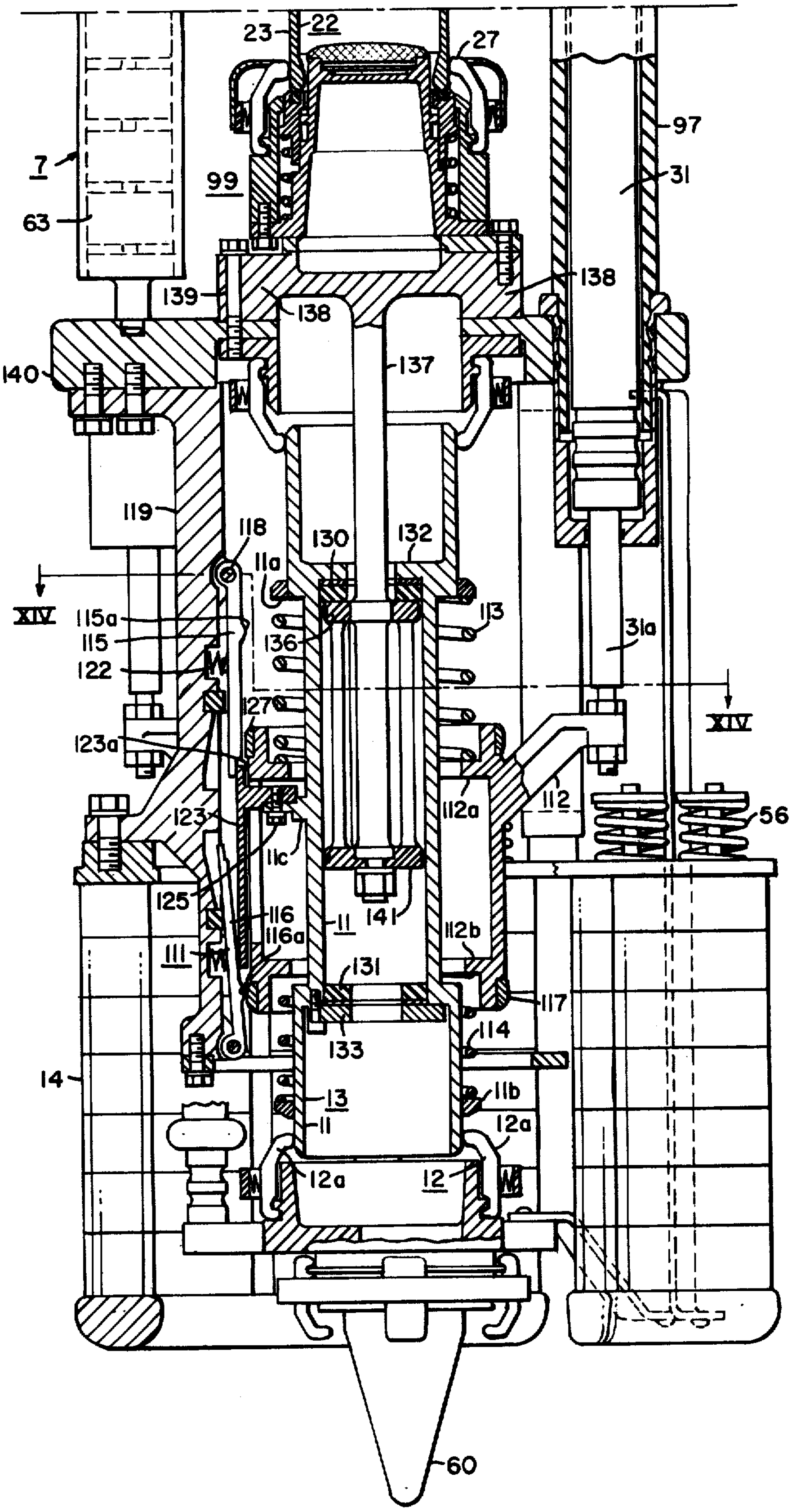
FIG. 7C is an enlarged vertical sectional view taken through the lower separable resistance contacts, the resistance contacts also being illustrated in the closed-circuit position.

In the closed-circuit position of the circuit-interrupter 1, as illustrated in FIGS. 7A, 7B and 7C, the circuit 16 is closed through the two columnar assemblages 3, 4, and the resistance 14 is out of the circuit, as caused by the closing of the shunting resistor contacts 11 and 12.

The shunting of the closing resistance 14 is, of course, desirable as well appreciated by those skilled in the art, inasmuch as it would lead to heating and energy losses in the closed-circuit position of the interrupter 1. Its use during the closing operation is to avoid the occurrence of high-voltage surges occurring on the line 16 during a closing operation. The theory and functioning of a closing resistance of the proper value is, of course, set forth in the aforesaid Van Sickle U.S. Pat. No. 3,291,947, to which reference has been made and the subject matter of which is incorporated herein by reference.

During the opening operation, it is, of course, desirable for the erosion and burning associated with the extinguishing of the arcs 18, 19 to occur only at the main two contact assemblages 21, 22 in the upper portion of the columnar arc-extinguishing assemblage 3.

Figure 12:
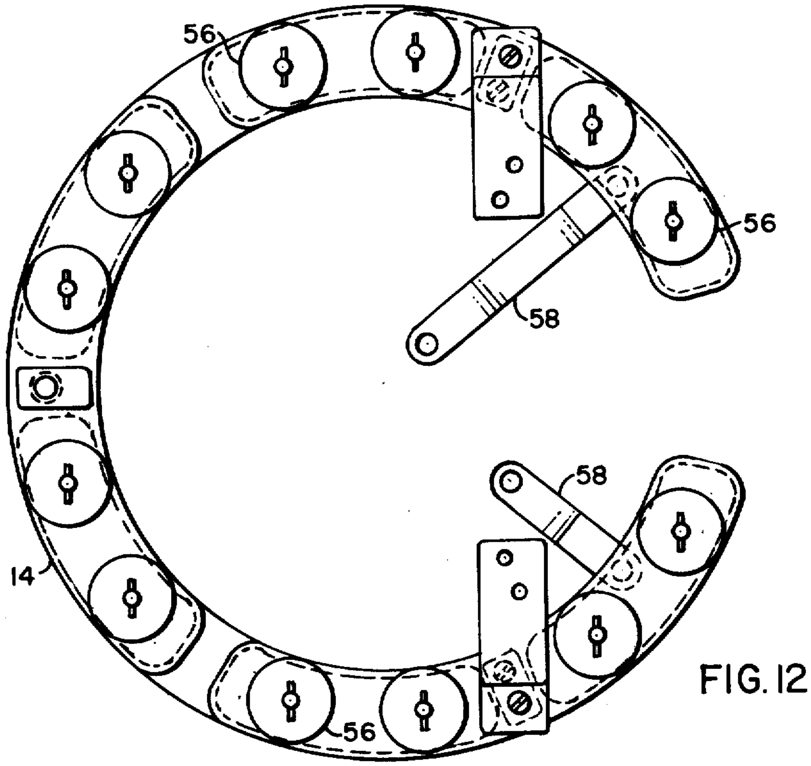
FIG. 12 is a top plan view of the closing-resistance assemblage of FIG. 13.
Figure 13:
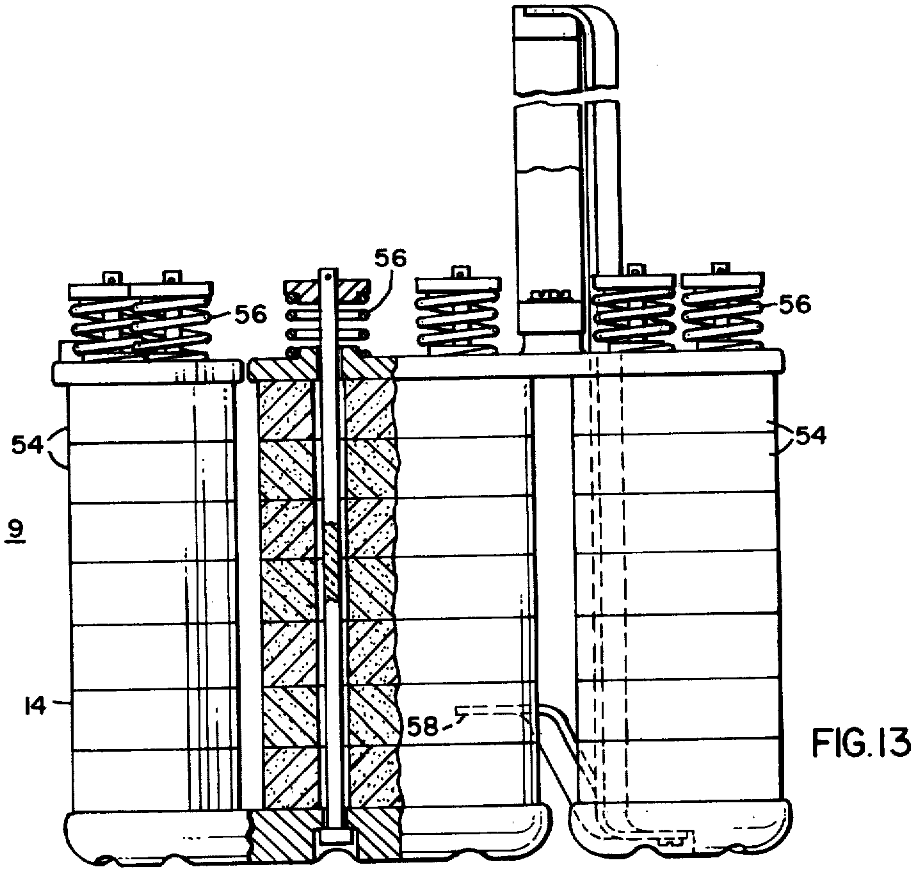
FIG. 13 is a generally side elevational view of the closing-resistance assemblage.

The closing resistance assemblage 14 is more clearly set forth in FIGS. 12 and 13, where it will be observed that the carbon arcuate segments 54 are in compression, as caused by the compression springs 56, and connections 58 between the carbon resistance segments cause the resistance assemblage 14 to be of the right ohmic value, as set forth in the aforesaid Van Sickle U.S. Pat. No. 3,291,947.

Figure 5B:
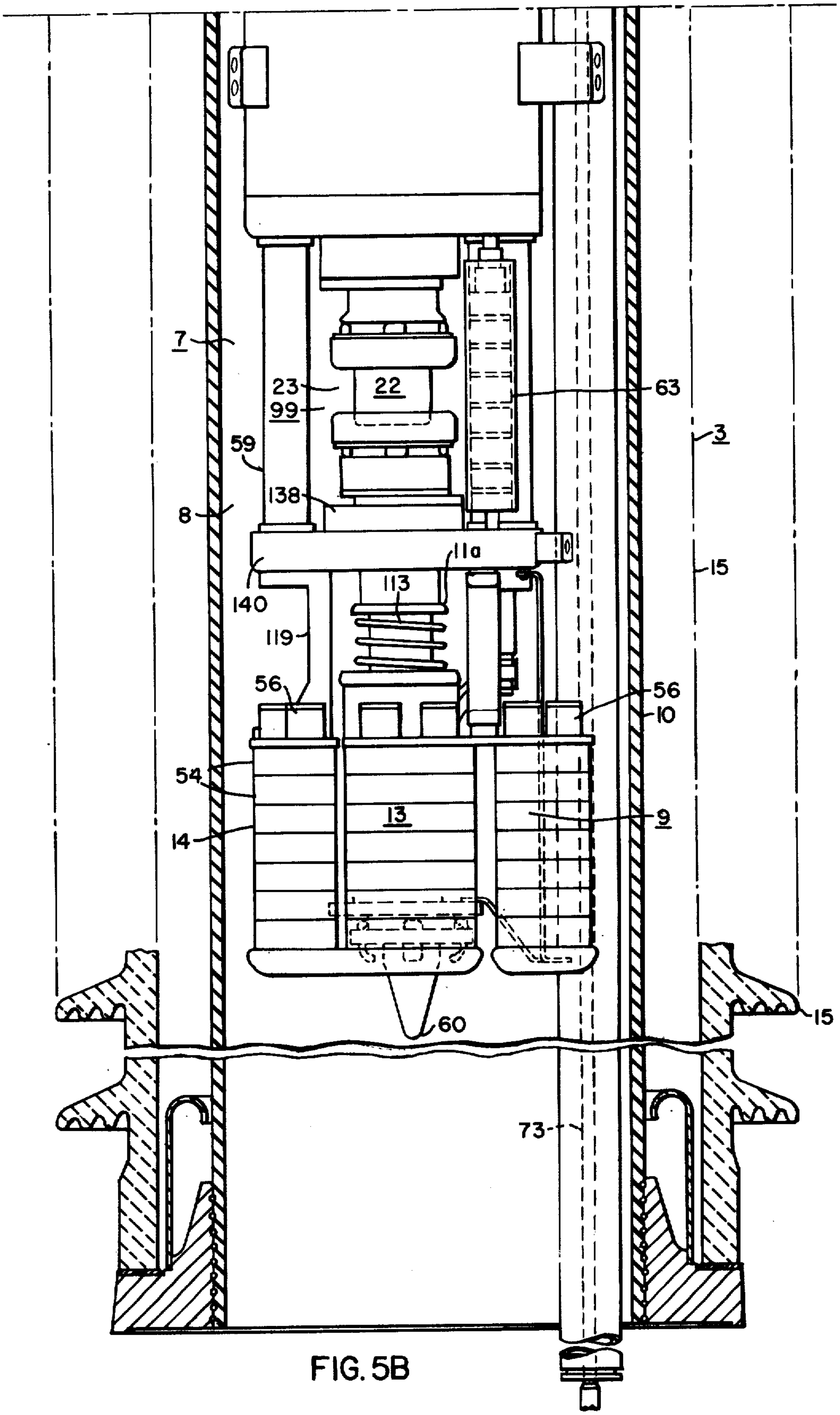
FIG. 5B shows the lower portion of the same breaker of FIG. 5A, again the contacts being shown closed.

With reference to the lower end of the columnar assemblage 3 it will be observed that there is a lower nose-shaped guide portion 60, which is guided into the upper open end of a generally U-shaped conductor tube, as indicated by the reference numeral 71 in FIG. 5B of the aforesaid Kane et al. U.S. Pat. No. 3,596,028.

Figure 9:
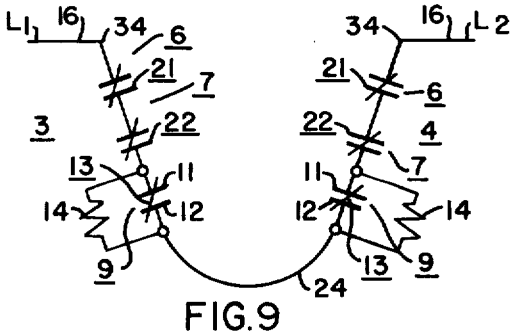
FIG. 9 is a diagrammatic view of the circuit illustrating the location and arrangement of the two main arc-extinguishing units for each side of the pole-unit, with an indication of the location of the closing-resistance contacts, and the relationship of the closing resistance relative to the separable resistance contacts, all of the contacts being illustrated in the closed-circuit position of the circuit-interrupter.

Although the above description has been centered around one columnar assemblage 3, it will be noted that the same description is appropriate for the other slantingly-arranged columnar arc-extinguishing assemblage 4, which has a generally identical construction and function. As a result, there are four main separable contact structures in each pole-unit "A", "B", or "C", as shown in FIG. 9. The function of these four main contact structures is to interrupt the electrical current flow through the pole-unit "A" during the opening operation, and the four separable main contact structures distribute the arcing 18, 19, and voltage division among the four series breaks is controlled by shunting capacitor branches paralleling the interrupting assemblages. These are designated by the reference numerals 62 and 63 of FIGS. 7A and 5B.

It is to be further noted that in each pole-unit "A", "B", or "C" there is provided the two closing resistances 14 (FIG. 9) together with their associated separable resistance contact assemblages 13, which function, during the opening operation, to keep the resistances 14 out of the circuit 16 during the interruption process. During the closing operation of the interrupter 1, on the other hand, the main contact structures 21, 22 are closed, whereas the separable resistance contacts 11, 12 are still open, so that the two resistances 14 are serially inserted into the circuit 16 during the closing operation to prevent high-voltage surges occurring on the line 16.

Figure 4:
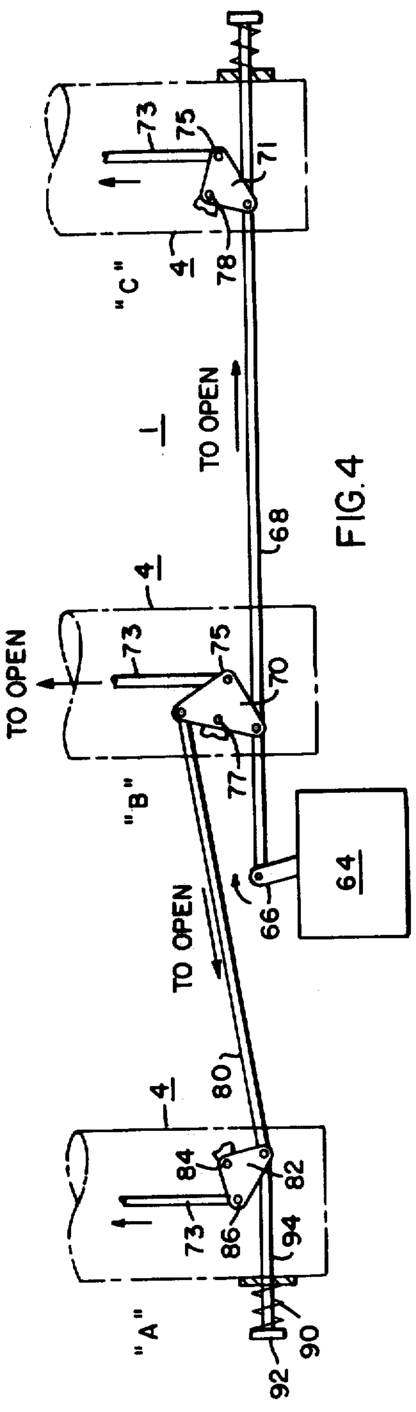
FIG. 4 is a somewhat diagrammatic view of the operating linkage and ground-potential mechanism for actuating the valve-tripping rods for pneumatically actuating the three pole-units of the three-phase gas-blast circuit-interrupter of FIG. 1, the valve-linkage being illustrated in the closed-circuit position of the circuit-interrupter.
Figure 10:
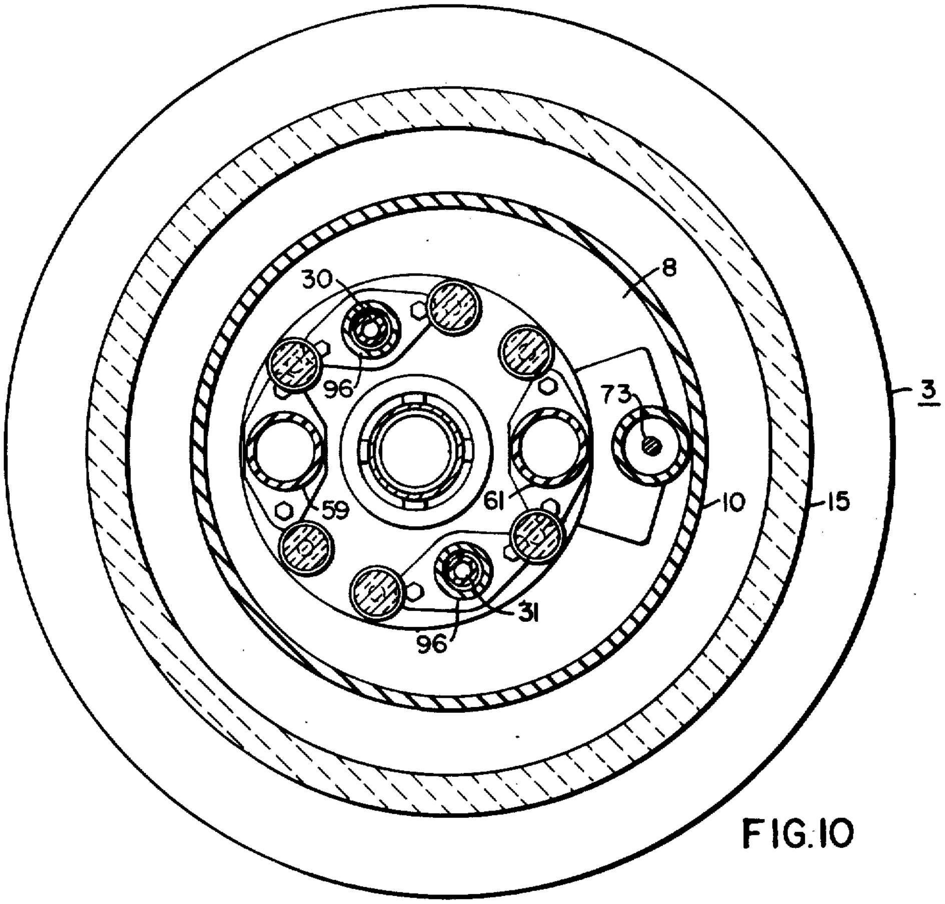
FIG. 10 is a sectional view taken substantially along the line X—X of FIG. 5A.
Figure 11:
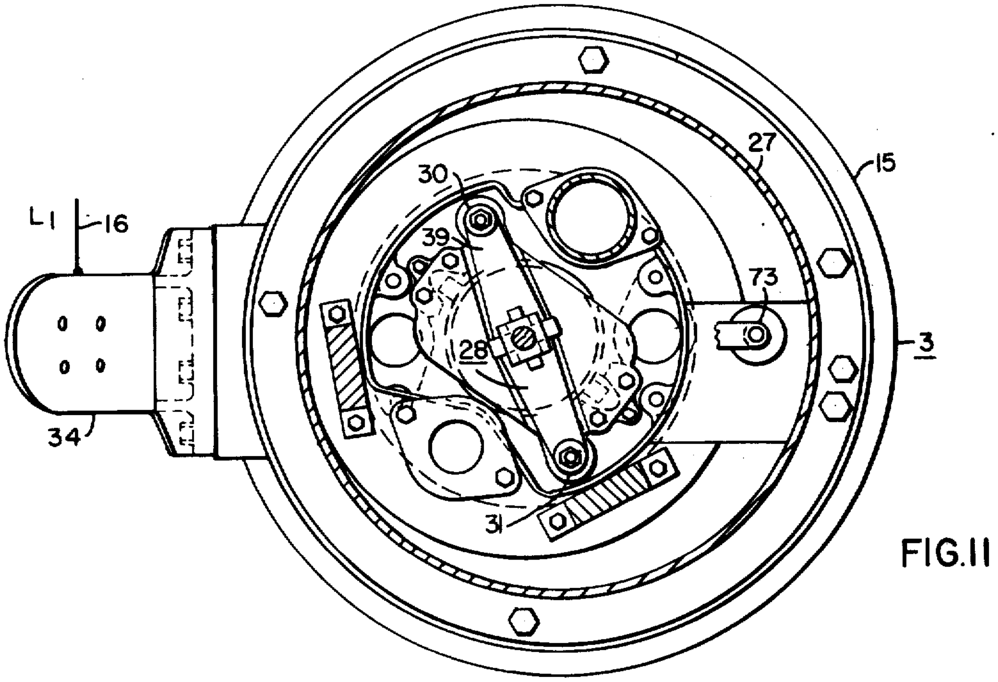
FIG. 11 is a sectional view taken substantially along the line XI—XI of FIG. 5A.

As set forth in FIG. 4, a main operating mechanism 64 at ground potential, which is described in U.S. Pat. No. 3,624,329, which issued Nov. 30, 1971 to Fischer et al, effects rightward movement of an operating lever 66, which, through a connecting rod 68, effects counterclockwise rotation of two bell-crank levers 70, 71, each of which has an upstanding movable valve-rod 73 (FIG. 10) pivotally connected thereto at 75. The two bell-crank levers 70, 71 are pivotally mounted on stationary pivots 77, 78. The central bell-crank lever 70 is pivotally connected, by a connecting rod 80, to the left-hand bell-crank lever 82, which moves in a clockwise direction about a stationary pivot 84. Pivotally connected at 86 to the left-hand bell-crank lever 82 is the upstanding valve-rod 73 associated with the pole unit "A".

An accelerating spring 90, shown in FIG. 4, bears against a cap portion 92 affixed to the left-hand extremity of a guide-rod 94, the right-hand end of the latter being pivotally connected to the left-hand bell-crank lever 82. Accordingly, clockwise pivotal rotation of the driving lever 66 effects upward movement of all three valve-rods 73, which serve to pneumatically cause pressure to occur on the top side of an operating piston (not shown) constituting a part of the operator 26 illustrated in FIG. 5A of the drawings.

The operator 26 is set forth and described in U.S. Pat. No. 3,590,189, and during the opening operation, as described hereinbefore, causes downward movement of the H-shaped frame 28 comprising the two operating rods 30, 31 movable within stationary guide sleeves, or tubes 96, 97, and serving to simultaneously cause the downward closing movement of the two main movable contacts 20, 23.

As set forth in U.S. Pat. No. 3,596,028, a latching arrangement 100 (FIG. 7A) is associated with each main movable contact 20 or 23. as disclosed more clearly in FIG. 6B of the drawings. It will be observed that there are provided a pair of pivotally-mounted latches 102 biased radially inwardly by a pair of compression springs 104, only one latch assembly 102 being viewed in FIG. 6B of the drawings. The construction is such that during the closed position, as viewed in FIG. 7A, the latches seat upon shoulder portions 106 associated with the secondary blast-valves 107, which, when open, permits gas flow to occur out ports 108 associated with the rear side of the upper movable main contact 20, as viewed in FIG. 6A. This gas-flow action is described in more detail in U.S. Pat. No. 3,596,028 to which reference may be made, and the subject matter of which is incorporated herein by reference.

Figure 6A:
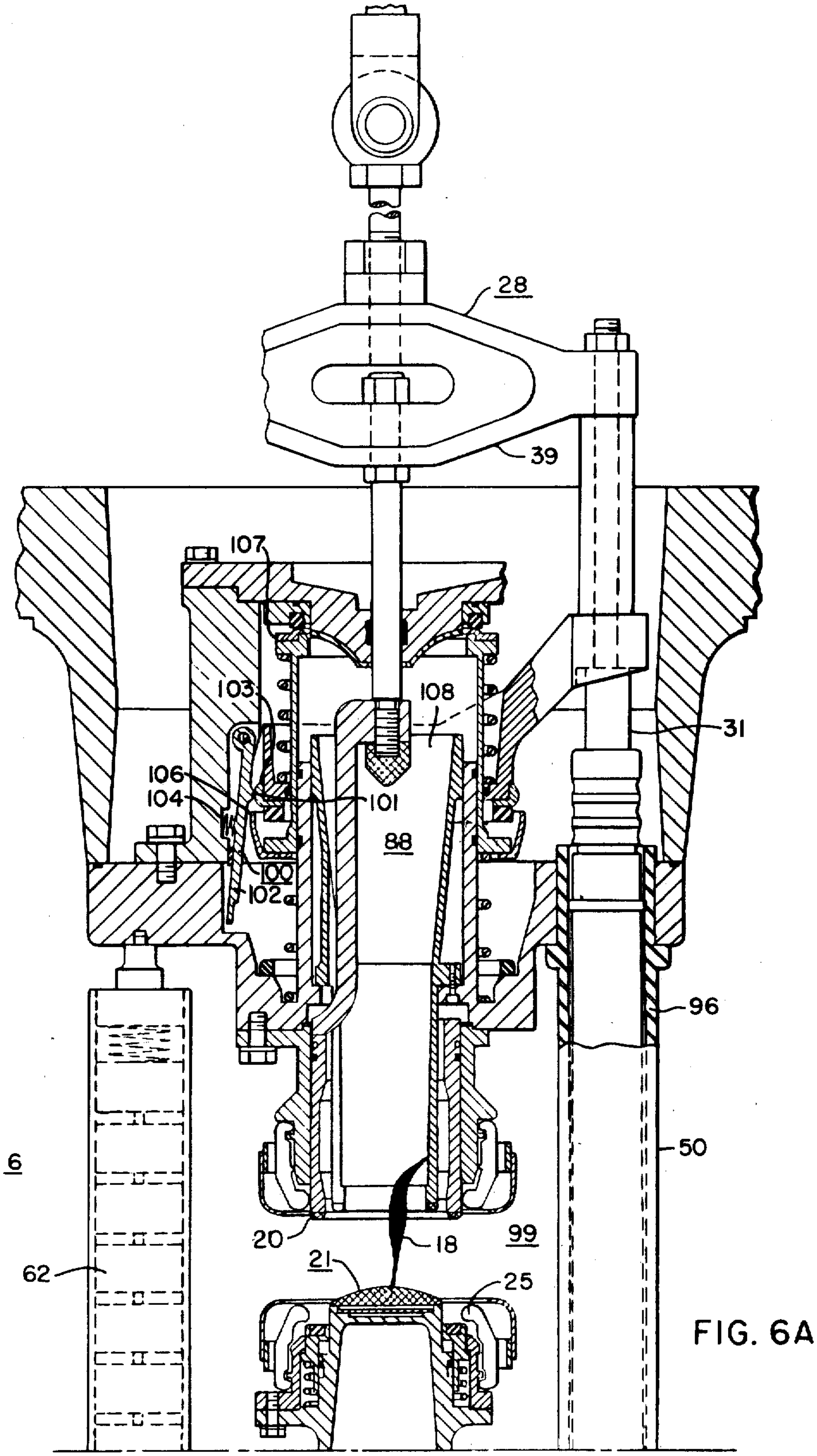
FIG. 6A is a vertical sectional view of the upper main contact structure for the upper main arc-extinguishing unit, the illustration showing the separable main contacts in the fully-open-circuit position.
Figure 6B:
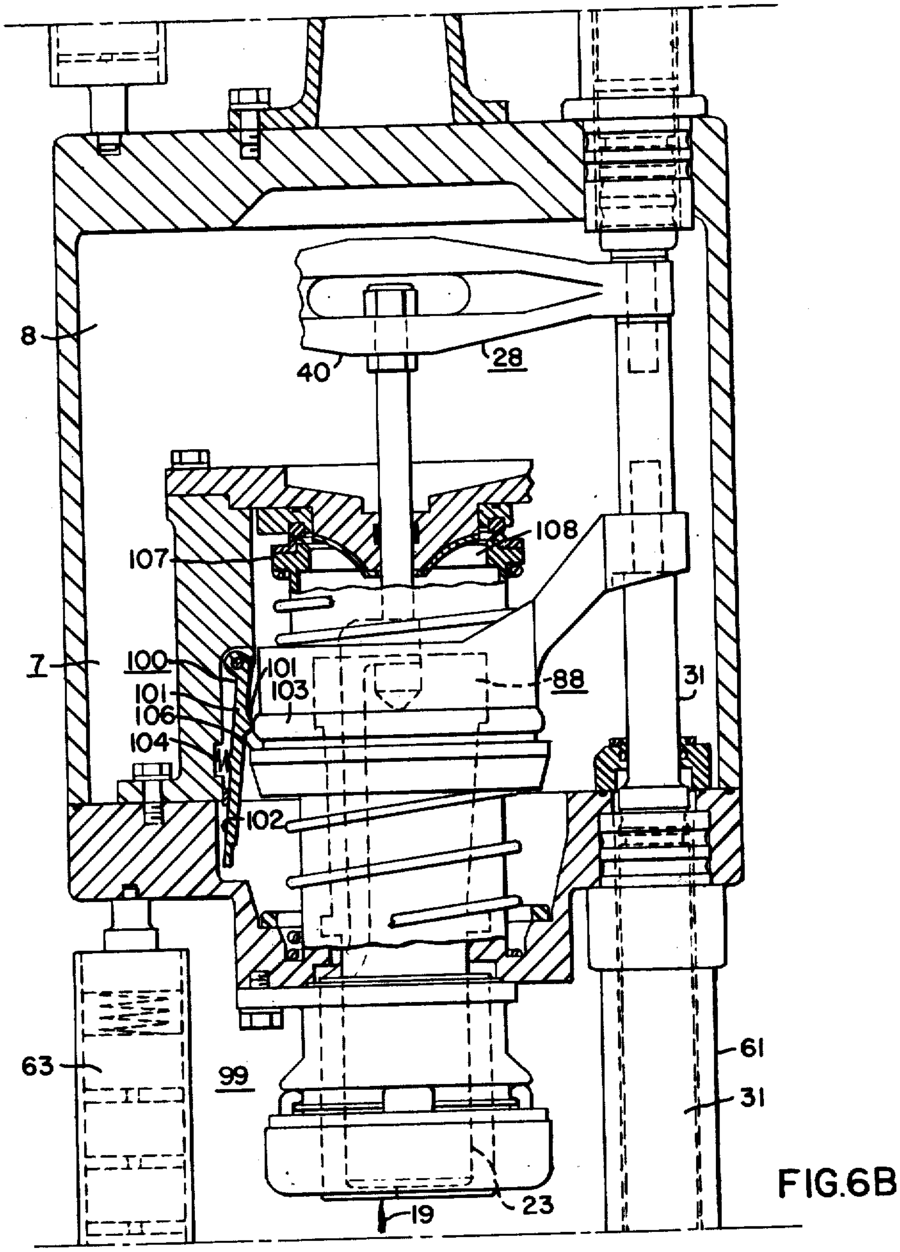
FIG. 6B is a fragmentary enlarged view of the lowermost main contact structure showing the latter in the fully-open-circuit position. It will be noted that this extinguishing structure is in series with the upper main contact structure shown in FIG. 6A.

Following a predetermined opening motion of the movable contact structure 20 or 23, a portion 103 of the movable contact structure bears on a cam portion 101 of the latches 102, forcing the latches 102 outwardly to thereby release the blast-valves 107, which move upwardly to the closed position, thereby halting any gas flow out of the interrupting chamber 88 (FIG. 6A) in the open position of the main contacts, as illustrated in FIGS. 6A and 6B of the drawings. It will be noted that there exists at all times high-pressure gas within the region externally of the main contact structure, as designated by the reference numeral 99 in FIG. 6B of the drawings. This high-pressure gas is available immediately upon separation of the contacts to effect extinction of the arcs 18, 19, which are indicated in the drawings, although the contact structure is illustrated in the fully-open position in FIGS. 6A and 6B of the drawings.

Figure 6C:
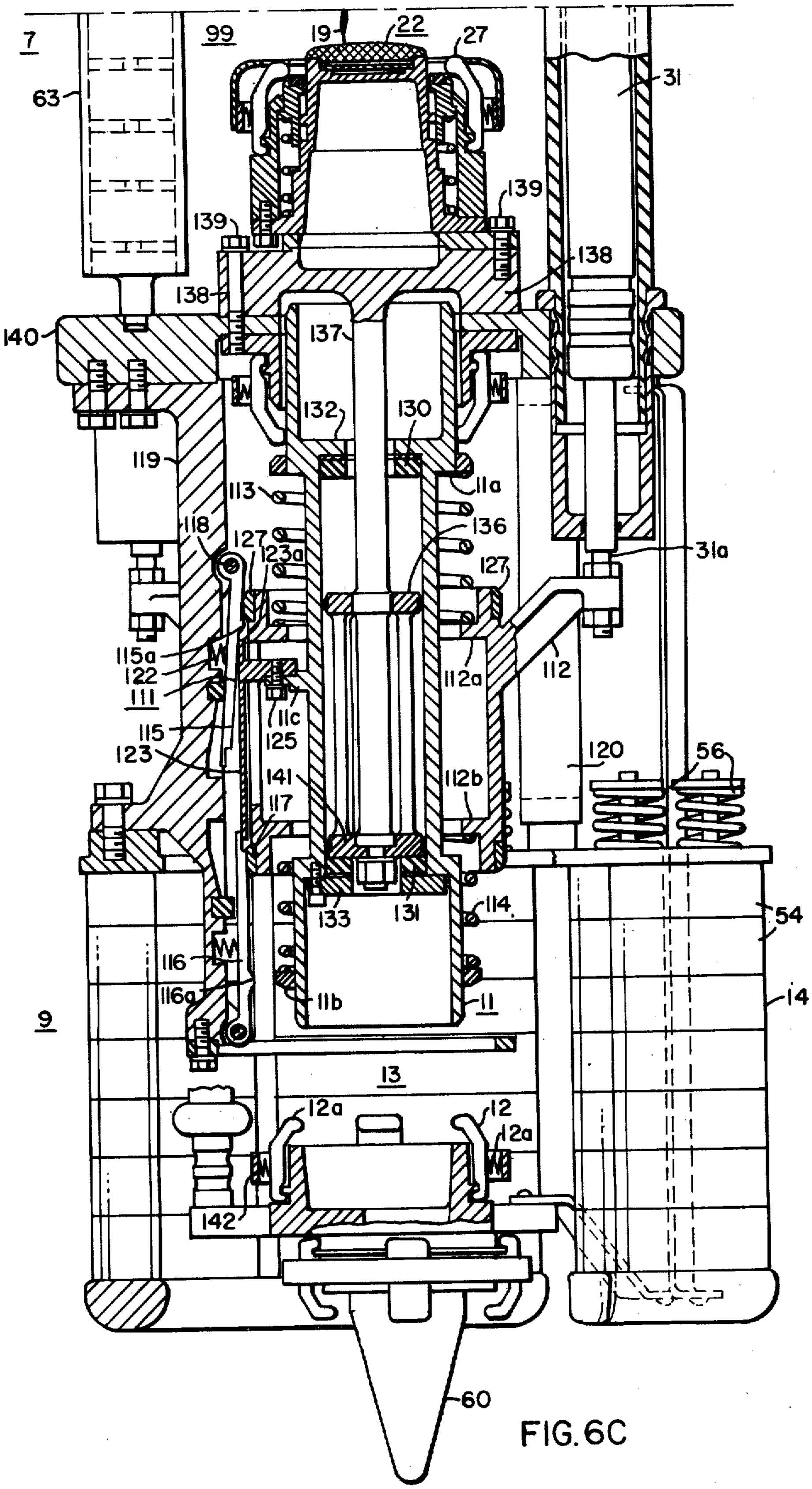
FIG. 6C is an enlarged vertical sectional view showing the separable resistance contacts with these contacts in the fully-open-circuit position of the interrupter.

FIGS. 6B and 7B show more clearly the mechanical interconnection of the movable main contact 23 of the lowermost main arc-extinguishing structure 7. It will be observed that a cross-member 40 is mechanically interconnected between the two operating rods 30, 31, and serves somewhat the same function as the upper traverse member 39 of FIGS. 6A and 7A. With reference to FIGS. 6C and 7C, it will be observed that the longitudinally-extending operating rods 30, 31 have attached to their lower ends **30*a*, 31*a* an activator casting, or driver member 112 of generally cylindrical construction, and having inwardly-extending annular flange portions 112*a* and 112*b* disposed adjacent the opposite ends thereof. The upper flange portion 112*a* forms a movable spring seat for an opening compression spring 113, which seats against a shoulder portion 11*a* of a movable resistance contact frame member, generally designated by the reference numeral 11**.

The lower flange portion **112*b* of the driver, or operator member 112 forms a movable spring-seat for a closing compression spring 114, which seats at its lower end against an outwardly-extending flange portion 11*b* fixedly secured adjacent the lower end of the movable resistance contact 11, as viewed in FIGS. 6C and 7C. Accordingly, it will be apparent that upward, or opening and downward, or closing movements of the activator casting, or operator member 112 will, depending upon the direction of movement thereof, effect compression or charging of either the opening spring 113, or, alternatively, charging of the closing spring 114. In other words, the activator member 112 will store compressive spring energy into either the opening spring 113 or the closing spring 114, depending upon the direction of movement of the driver member 112, as caused by the direction of movement of the longitudinally-extending operating rods 30, 31, the latter, of course, being connected through frame members 39, 40 to the two main movable contacts 20, 23 of the main arc-extinguishing interrupting units 6, 7**.

A pair of closing latches 115 are pivotally mounted upon stationary pivots 118, as afforded by a pair of stationary frame members 119, 120, and are biased radially inwardly by small compression springs 122, so that the closing latches 115 latch into key portions **123*a* of a key member 123, which is fixedly secured by mounting bolts 125 to an outwardly-extending flange portion 11*c* of the movable resistance contact 11. Accordingly, when the main longitudinally-extending operating rods 30, 31 move upwardly, as viewed in FIGS. 6C and 7C, the closing latches 115 retain the movable resistance contact 11 in its closed position, as viewed in FIG. 7C, until a ring-shaped bumper portion 127, movable with the activator member 112, strikes a protrusion portion 115*a* of the pivotally-mounted closing-latch 115 and unlatches the same from the key portion 123*a* of the key member 123, secured to the movable frame 11*b* of the resistance contact 11 thereby allowing the stored energy in the opening spring 113 to effect rapid opening of the movable resistance contact 11 to its fully open-circuit position, as illustrated in FIG. 6C**.

Similarly, during the closing operation of the interrupter 1, it is desirable to momentarily insert the closing resistance 14 into the circuit 16 following closing of the two main contacts 20, 23 for a short interval of time prior to a subsequent closing of the movable shunting resistance contact 11 into its closed position, as shown in FIG. 7C. in other words, during a closing operation, it is desirable to have the closing resistance 14 serially connected into the electrical circuit 16 to damp high-voltage surges on the controlled circuit 16, and to effect this end it is desirable to bring about the closing of the two main movable contact structures 6, 7, yet delaying the closing movement of the movable resistance contact 11, which would, obviously, short out the closing resistance 14. Consequently, for a short period of time, as determined by the latch construction 111, the closing resistance 14 will be inserted serially into the circuit 16 during the closing operation and finally shorted out by a delayed closing movement of the movable resistance contact 11.

The length of time that the movable resistance contact 11 is delayed during its opening and closing movements is brought about by the physical dimensions and locations of the two pairs of latches 115 and 116, the former being closing latches and the latter two latches 116 being opening latches to delay the opening and closing movements of the movable resistance contact 11.

To cushion the opening and closing movements of the movable resistor contact 11, a pair of rubber or resilient bumpers 130 and 131 are fixedly secured to flange portions 132 and 133 of the movable resistance contact 11, so that in the closed position of the movable resistance contact 11, the ring-shaped bumper 130 movable with the resistance contact 11, strikes a stationary ring-shaped stop 136 affixed to a stationary inwardly-extending rod 137 fixedly secured to the end support flange 138. The end support flange 138 is secured by mounting bolts 139 to an end-plate support member 140, as illustrated in FIGS. 6C and 7C.

Similarly, at the end of the opening movement of the movable resistance contact 11, the ring-shaped resilient bumper 131, affixed to and movable with the movable resistance contact 11, will strike a second ring-shaped stop 141 also fixedly secured to the central protruding support rod 137.

As well known by those skilled in the art, to carry the heavy load currents associated with a circuit-interrupter of the high-voltage type, a plurality of stationary finger contacts **12*a*, biased inwardly by compression springs 142, make good spaced contacting engagement with the outer surface of the cylindrically shaped movable resistance contact 11, as illustrated in the closed position of the resistance contact 11 illustrated in FIG. 7C**.

From the foregoing description it will be apparent that the resistor activator cylinder member 112 is directly mechanically connected to the same operating rods 30, 31, which control the opening and closing movements of the two main movable arcing contacts 20, 23 of the two extinguishing units 6, 7. The resistor activator unit 9 is constructed with the protrusion **116*a* on latch 116 such a location that the movable resistor contact is delayed the proper amount of time so as not to unduly heat the resistor assembly 14 during the closing operation. Movement of the resistor activator member 112 alternately compresses the opening spring 113, or the closing spring 114 during the corresponding opening and closing movements of the drive or activator member 112, as controlled from the main high-voltage operating mechanism 26. The latches 115, 116 insure that the movable resistance contact 11 is retained in either its open or closed-circuit positions until the proper time has elapsed for shorting out the closing resistance 14 during the closing operation, or making sure that the separable resistance contacts 11, 12 have maintained adequate contact until all arcing is out in the two main arc-extinguishing units 6, 7 during the opening operation of the interrupter 1**.

Also, it will be observed that energy is stored, alternately, in either the closing spring 114 or the opening spring 113, and is subsequently used, following release of the latches 115, 116, to effect quick-opening and closing movements of the movable resistance contact 11, as illustrated in the open and closed positions of the movable resistance contact 11, as viewed in FIGS. 6C and 7C. Delay of time from the main contact opening to the resistor contact opening is a function of the location of the protrusions 115*a*, or latch 115. The length of travel of the bevel 127 on the movable activator 112 to meeting the protrusion 115*a* on the latch member 115 provides the correct length of time. This is a positive delay to assure time for interruption of the electrical circuit in the main extinguishing units 6, 7 while assuring that the resistance 14 is shorted out in the interruption process. Thus, this time delay guarantees that no burning or erosion of the resistor-contact 11 or resistor contact fingers 12 will occur during the opening operation.

During the closing operation, the time delay of the resistor contact 11 closing after the main contacts 20, 23 close is also a function of the position of the protrusion 116*a* on the latch element 116. The main contacts 20, 23 are thus closed so that the resistor 14 is serially inserted into the circuit 16 during the closing operation, which is desirable, to eliminate, or avoid high-voltage surges occurring on the controlled electrical line 16.

Also, the time that the closing resistance 14 is in the circuit 16 during the closing operation is positively controlled to limit the temperature rise within the closing resistor elements 14.

The opening and closing springs 113 and 114 also control the mass movement of the movable resistance contact 11 on both the opening and closing operations. The characteristics of the opening and closing springs 113 and 114 would, of course, determine the velocity of the opening and closing movements of the movable resistance contact 11, as will be obvious.

Figure 8:
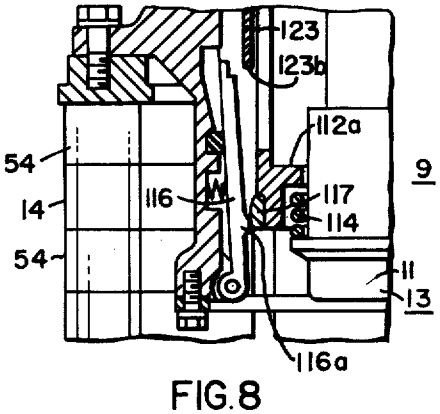
FIG. 8 is a fragmentary view illustrating the conditions during a closing operation when the latch for the movable resistance contact is just released to permit a quick closing of the movable resistance contact.

FIG. 8 shows a fragmentary view of the separable closing resistance contacts at the point where the bumper 117 strikes the protrusion 116*a* on pivotally-mounted latch 116, and permits the movable resistance contact 11 to quickly close under the biasing action exerted by its closing spring 114.

Also associated with each columnar assemblages 3, 4 is an outer cylindrical insulating casing member 10, which holds the high-pressure gas 8 within the regions 99 externally of the two main contact structures 21, 22. Also, it will be noted that externally of the insulating casing member 10 is disposed an outer porcelain casing 15 utilized for its weatherproof characteristics. Suitable means, not shown particularly, and not pertinent to the present invention, are provided for applying compressive force on the outer porcelain casing member 15 and corresponding tensile stress upon the inner insulating tubular casing 10. The upper line connection $L_1$ is secured to a terminal structure 34 more clearly shown in FIG. 5A, which electrically connects the circuit 16 to the uper main movable contact 20. As set forth in the aforesaid Kane et al U.S. Pat. No. 3,596,028, the circuit 16 extends through both columnar assemblages 3, 4 and terminates at the upper end 34 of the other assemblage 4 of FIG. 1.

In the device of our invention, there is a total closing travel distance of approximately 3 inches, for example, of the two main movable arcing contacts 20 and 23. After approximately 2¼ inches of closing travel of the two main movable contacts 20 and 23, at this point in time the latches 116 are released by the camming movement of the cam 117, affixed to the activator member 112. Thus, the upper two main movable contacts 20, 23 are closed when the latches 116 are released, so that there is a momentary insertion of the closing resistance 14 into the circuit 16 prior to the subsequent, in point of time, closing of the resistance contacts 11 and 12. This adjustment is, of course, variable depending upon the desires of the utility customer, and the above travel distance is given only by way of example, and not by way of limitation.

During the opening operation of the circuit-interrupter 1, the upper two movable main contacts 20, 23 have traversed substantially 2¼ inches of their 3-inch total travel distance by the time that the opening latches 115 are tripped. Thus, in effect, the two upper movable main contacts 20, 23 are in the fully open-circuit position at the point in time at which the opening latches 115 are released to thereby permit a following delayed opening movement of the lower movable resistance contact 11.

Figure 15:
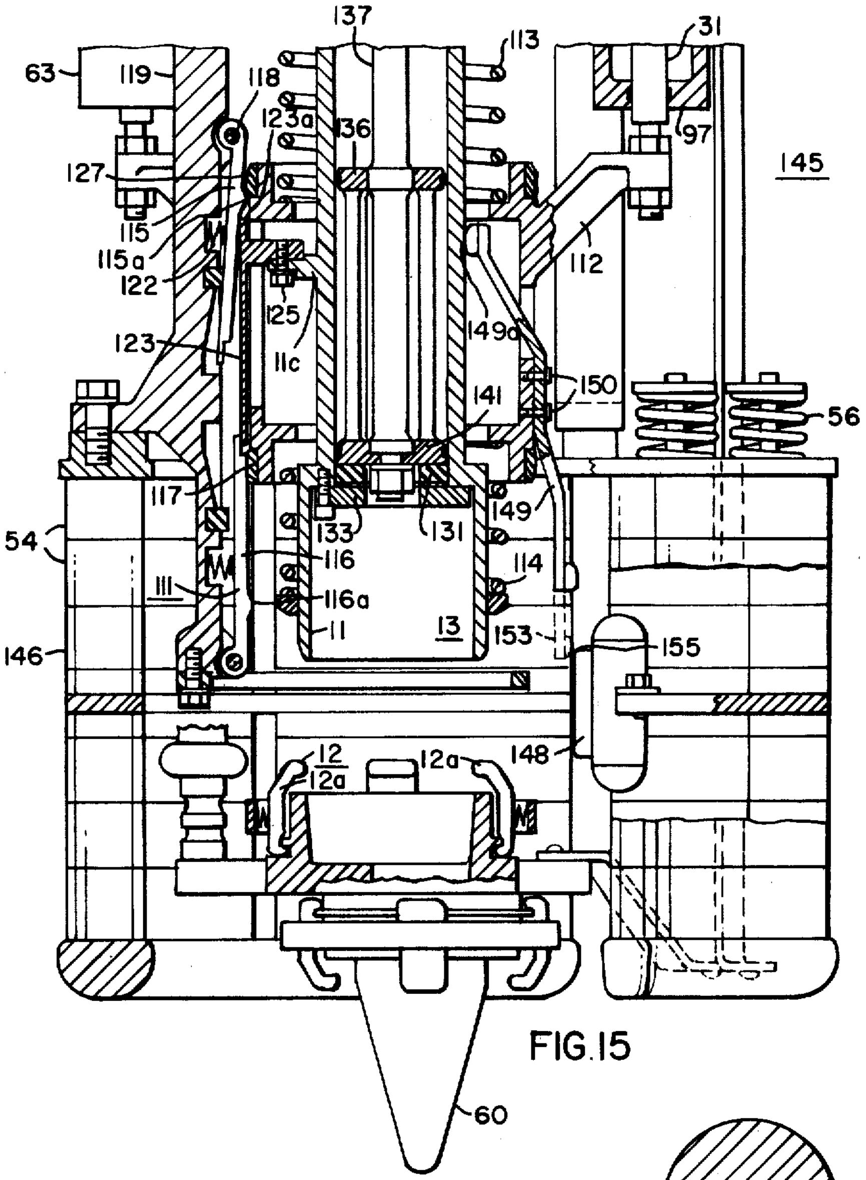
FIG. 15 is a vertical sectional view taken through a modified-type of interrupting unit utilizing a two-step closing resistance construction, the figure showing the separable resistance contacts in their fully open-circuit position.
Figure 17:
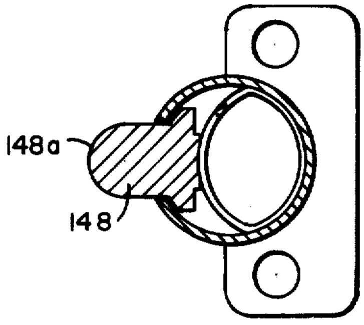
Figure 16:
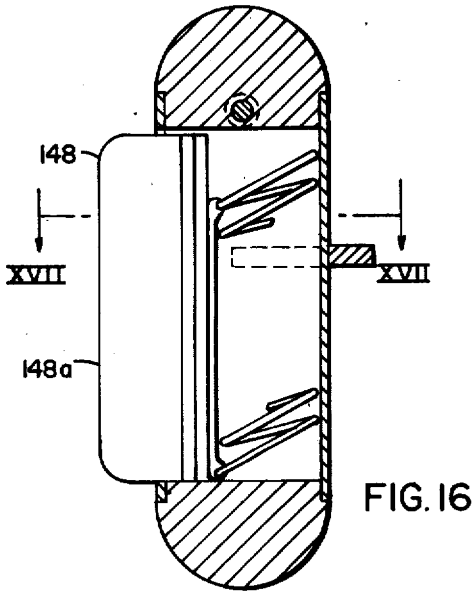
FIG. 16 is an enlarged view of the stationary sliding probe resistance contact utilized in the modified interrupter construction of FIG. 15, drawn to an enlarged scale; and, FIG. 17 is a sectional view taken substantially along the line XVII—XVII of FIG. 16.

FIGS. 15–17 illustrate a modified-type of circuit-breaker construction 145 in which a two-step closing resistance 146 is utilized. With particular attention directed to FIG. 15 of the drawings, it will be observed that there is provided a stationary probe resistance contact 148, which, at times, makes sliding contacting engagement with a movable probe contact 149, which is affixed, by mounting bolts 150, to the movable activator, or operating member 112.

The upper end of the strap-like moving probe contact 149 contains a finger contact 149*a*, which makes sliding contact on the outer side surface 11*c* of the movable main resistor contact 11.

FIG. 15 illustrates the position of the several parts in the fully open-circuit position of the circuit-interrupter 145. During a closing operation of the interrupter 145, the activator 112 moves downwardly carrying with it the moving probe contact 149. At the position, indicated by the dotted lines 153, indicating the position of the moving probe contact 149, at this point in time the main contact structures 21 and 23 are closed, thereby inserting the full value of the closing resistance 146 into the circuit 16.

It is to be noted that the point in time at which the release of the closing latches 116 occurs is also substantially the point in time at which the main contacts 21, 23 close. As mentioned, the dotted position 153 of the moving probe contact 149 is the point in time at which the main contacts 21, 23 make engagement, and thereby insert the full value of the closing resistance 146 into the circuit 16.

With reference to the dotted position of the moving probe contact 149, it will be observed that there is a gap 155 between the moving probe contact 149 and the stationary probe resistance contact 148. This is to insure that the full value of the closing resistance 146 is inserted into the circuit 16. However, continued downward closing movement of the activator 112 will cause the moving probe contact 149 to make sliding engagement with the stationary probe resistance contact 148, thereby shorting out substantially half of the closing resistance 146. Also, as mentioned, the unlatching of the moving resistance contact 11 will effect closure of the separable resistance contacts 11, 12, thereby completely shorting out the closing resistance 146.

From the foregoing it will be apparent that there is a short period of time that the full value of the resistance 146 is in the circuit 16, and then shorted out in two steps, the first step occurring upon engagement of the moving probe contact 149 with the stationary probe resistance contact 148, and the second step being shorted out by the closure of the main separable resistance cntacts 11, 12.

From the foregoing description it will be apparent that a novel arrangement has been provided, in connection with a closing resistance 14 and associated separable resistance contact structure 13, controlling the insertion of the closing resistance 14 into the circuit 16 only during the closing operation of the breaker 1. During the opening operation of the breaker, the closing resistance 14 is deliberately shorted out of the circuit 16, so that the full burden of arc-extinction 18, 19 is imposed only on the upper two main separable contact structures 21, 22, and no arcing occurs at the separable resistance contacts 11, 12.

Suitable mechanical support tubes 50, 61 are provided to fixedly maintain the stationary contact structures 25, 27 in the desired stationary location, and to provide mechanical integrity of the arc-extinguishing assemblage 3 as a whole.

Figure 2:
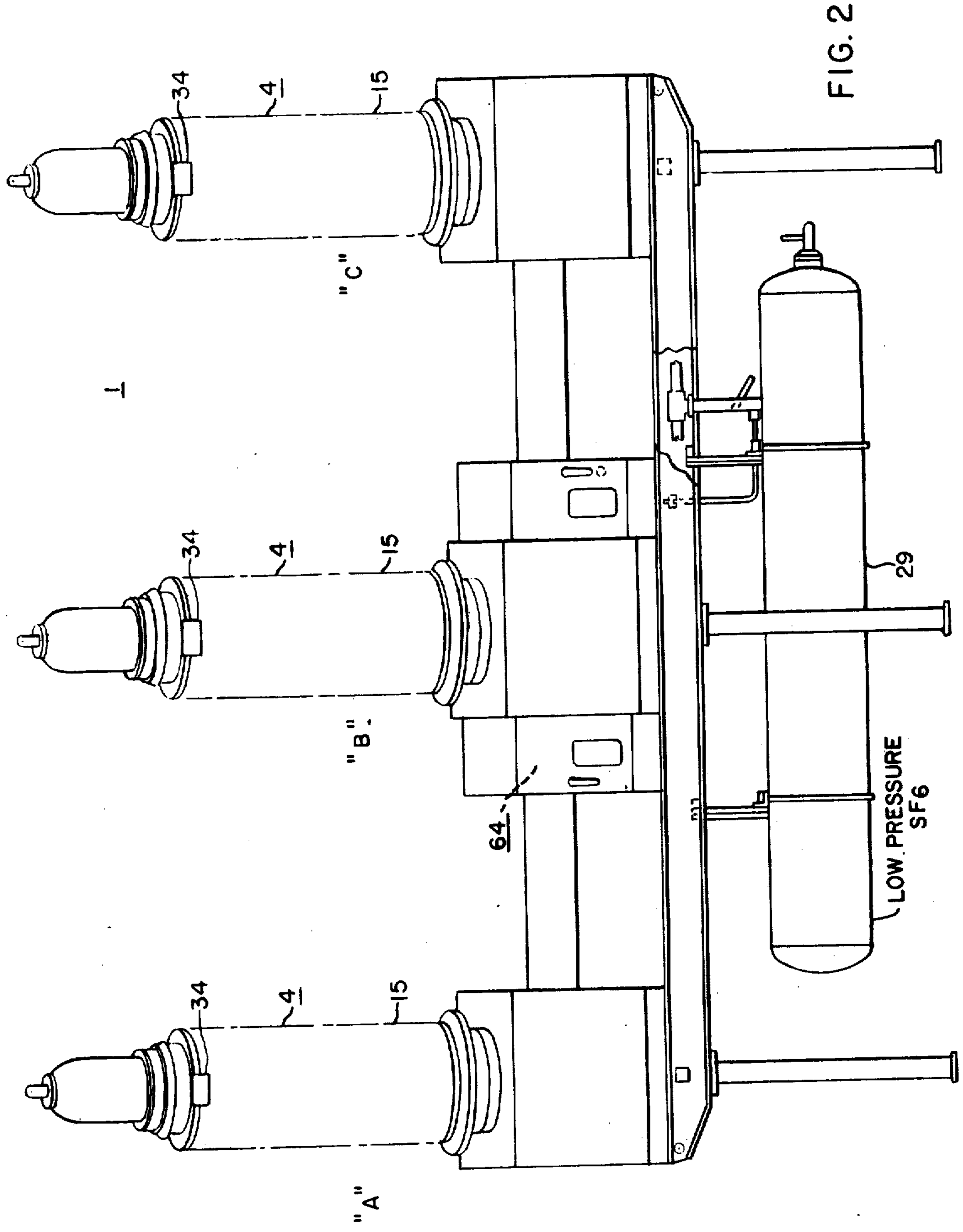
FIG. 2 is a side-elevational view of the three-phase gas-blast circuit-interrupter of FIG. 1.
Figure 3:
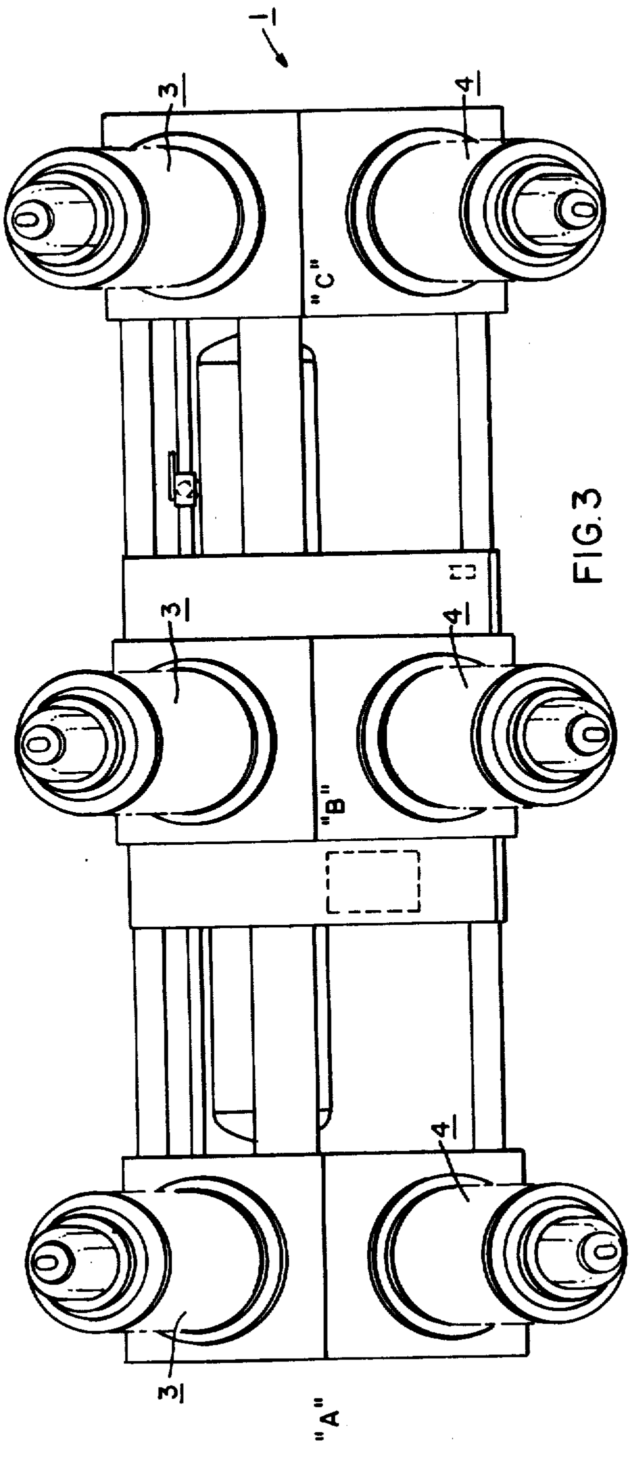
FIG. 3 is a top plan view of the three-phase gas-blast circuit-interrupter of FIGS. 1 and 2.

With reference to FIG. 2 it will be observed that a low-pressure tank 29 is provided together with compressor equipment, as set forth in U.S. Pat. No. 3,596,028. The high-pressure reservoir for providing high-pressure in the regions 99 around the separable main contact structures 21, 22 are provided within the U-shaped connecting tube 71 of FIG. 5B of U.S. Pat. No. 3,596,028, the subject matter of which is incorporated herein by reference.

The manner of arc-extinction and the operation of the various parts is also more clearly set forth in the aforesaid U.S. Pat. No. 3,596,028.

Closing resistors 14 are used on power circuit-breakers to limit or dampen switching surges on the circuit-breakers. Conventional circuit-breakers, without closing resistors, can produce switching surces of approximately 3.9 per unit (3.9 times the line-to-ground voltage for the particular voltage-class circuit-breaker being used). Circuit-breakers, using single-step closing resistors, can limit switching surges to approximately 2 per unit. The use of a two-step closing resistor can further limit the switching surges to approximately 1.7 per unit. Lower switching surges could possibly enable the use of circuit-breakers with lower basic insulation level ratings.

By the addition of a probe-assembly, as shown in FIG. 15 the basic one-step closing-resistor design of FIGS. 5 and 6 can be converted to a two-step resistor design as shown in FIG. 15. The two-step resistor design of FIG. 15 has a total resistor insertion time of approximately 0.50 cycles. An example of a two-step resistor condition would be 1200 ohm initial total resistance and 300 ohm resistance in circuit after the probe assembly has made contact and shorted out approximately 900 ohms. This happens at approximately 0.25 cycles after the main contacts 20 and 23 make contact. by converting from the single-step design to the two-step design, the switching surges can be reduced from approximately 2 per unit to approximately 1.7 per unit.

RESISTOR CONTACT SHIELDINGS

The resistor contact assembly 13 covered by this invention is encircled by the closing resistor 14.

From the foregoing description it will be apparent that there has been provided an improved mechanical control means, or mechanism for providing the correct time delay for controlling the opening and closing movements of the movable resistance contact 11 by appropriate latching means 111, and a storage of energy in opening and closing biasing means 113, 114. The time delay can be accurately controlled so that all arcing occurs on the main contacts 20, 23 and not at the resistor contacts 11, 12 during the opening operation of the breaker. Similarly, the desirable advantage is achieved of inserting the closing resistance 14 into the circuit 16 during the closing operation for the correct length of time prior to a subsequent shorting out of the closing resistance 14 by the closing of the resistance contacts 11, 12. Again the length of time may be accurately controlled. Also a two-step closing resistance may be utilized, as desired. Finally, the resistance assemblage provides a desired voltage gradient effect in shielding the resistor contact assembly.

Although there has been described a specific structure, it is to be clearly understood that the same was merely for the purpose of illustration, and that changes and modifications may readily be made therein by those skilled in the art without departing from the spirit and scope of the invention.

What is claimed is:

1. A high-voltage circuit-interrupter of the type for eliminating high-voltage surges on the controlled line comprising, in combination:

a. means defining a separable pair of main contacts including a movable main contact;

b. an operator for effecting the opening and closing motions of said separable pair of main contacts;

c. means defining a separable pair of resistance contacts including a movable resistance contact disposed in electrical series relationship with said separable pair of main contacts so that in the closed-circuit position of the circuit interrupter the line current passes serially through the two pairs of separable contacts;

d. means defining a closing resistance connected electrically in shunt with said separable pair of resistance contacts so that when said separable pair of resistance contacts are closed the closing resistance is shorted out of the controlled circuit;

a first biasing means for biasing said movable resistance contact to the closed-circuit position;

a second biasing means for biasing said movable resistance contact to the open-circuit position;

said operator including a movable activator member movable in the opening and closing directions and correspondingly charging said first and second biasing means during such opening and closing movements;

a first latching means for retaining the movable resistance contact in the closed-circuit position;

a second latching means for retaining the movable resistance contact in the open-circuit position;

latch-releasing means responsive to movement of said movable activator member and functioning alternatively to release the first and second latching means at predetermined times during the opening and closing movements of said movable activator member;

and means effecting the closing of the separable pair of main contacts during the closing operation of the circuit interrupter prior in point of time to the closing of the separable pair of resistance contacts so that the closing resistance is connected serially into the controlled circuit during the closing operation and subsequently shorted out by the delayed closing of the separable resistance contacts, whereby high-voltage surges on the controlled line tend to be eliminated.

2. The combination according to claim 1, wherein at least one of the biasing means includes a compression spring which is charged during movement of the movable activator member, and the latching means includes a rotatable latching lever biased into latching engagement.

3. The combination according to claim 2, wherein the first and second biasing means comprises an opening compression spring and a closing compression spring.

4. The combination according to claim 1, wherein the latch releasing means includes a pair of spaced cam members affixed to and movable with the movable activator member.

5. The combination according to claim 1, wherein the first and second latching means comprises pairs of latches located diametrically on opposite sides of the movable resistance contact.

6. The combination according to claim 1, wherein a stationary probe electrically connected intermediate the ends of the closing resistance makes sliding contact with the movable resistance contact during its closing operation.

7. The combination according to claim 1, wherein the movable resistance contact comprises a generally cylindrically-shaped member having spaced inwardly-extending flange portions carrying opening and closing bumpers;

and a stationary elongated stop member engages said opening and closing bumpers during the opening and closing operations of the circuit-interrupter.

8. The combination according to claim 7, wherein said movable resistance contact has a rearwardly-extending contacting portion and a plurality of circumferentially-spaced contact-fingers engage said rearwardly-extending portion during the opening and closing movements of the movable resistance contact.

9. A high-voltage circuit-interrupter of the type for eliminating high-voltage surges on the controlled line comprising, in combination:

a. means defining a separable pair of main contacts including a movable main contact;

b. an operator for effecting the opening and closing motions of said separable pair of main contacts;

c. means defining a separate separable pair of resistance contacts including a movable resistance contact disposed in electrical series relationship with said separable pair of main contacts so that in the closed-circuit position of the circuit interrupter the line current passes serially through the two pairs of separable contacts;

d. means defining a closing resistance connected electrically in shunt with said separate separable pair of resistance contacts so that when said separable pair of resistance contacts are closed the closing resistance is shorted out of the controlled circuit;

and movable probe means (149) electrically connected to one of the resistance contacts and making, at times, electrical engagement with a stationary probe resistance contact (148) so that the closing resistance may be shorted out in two steps during the closing operation of the interrupter.

10. The combination according to claim 1, wherein the closing resistance is divided into two steps by a relatively stationary probe resistance contact, and, a movable probe contact 149 moves with said activator member to short out, in succession, the two steps of the closing resistance.

11. A high-voltage circuit-interrupter of the type for eliminating high-voltages surges on the controlled transmission line comprising, in combination:

means defining a longitudinally extending casing structure, means defining an elongated arc extinguishing assemblage disposed within said casing structure comprising at least two pairs of serially related separable contacts, said two pairs of separable contacts being disposed in axial longitudinal alignment, longitudinally extending operating rod means for effecting substantially simultaneous movement of said two pairs of separable contacts which are in alignment, one of said separable pairs of contacts being a pair of separable main contacts, the other of said separable pairs of separable contacts being a pair of separable closing resistance contacts, means defining a shunting closing resistance assemblage shunting said pair of separable resistance contacts, and, said closing resistance assuming the form of a generally-cylindrically-shaped resistance assemblage encompassing said pair of separable closing resistance contacts, whereby longitudinal space of said assemblage is conserved.

12. The combination according to claim 11, wherein said closing resistance assemblage has an intervening contact probe (148), and a movable probe contact moves with the movable closing resistance contact for making intermittent contacting engagement with said first-mentioned contact probe (148) during the closing operation of the circuit interrupter to provide thereby a two-step closing resistance sequence.

* * * * *